United States Patent
Hasko et al.

(10) Patent No.: US 9,987,336 B2
(45) Date of Patent: Jun. 5, 2018

(54) ATTENUATING OR TREATING SEPSIS OR SEPTIC SHOCK

(71) Applicant: Rutgers, the State University of New Jersey, New Brunswick, NJ (US)

(72) Inventors: Gyorgy Hasko, Gillette, NJ (US); Zoltan Nemeth, Randolph, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days. days.

(21) Appl. No.: 14/420,462

(22) PCT Filed: Aug. 9, 2013

(86) PCT No.: PCT/US2013/054267
§ 371 (c)(1),
(2) Date: Feb. 9, 2015

(87) PCT Pub. No.: WO2014/026078
PCT Pub. Date: Feb. 13, 2014

(65) Prior Publication Data
US 2015/0209413 A1 Jul. 30, 2015

Related U.S. Application Data

(60) Provisional application No. 61/681,837, filed on Aug. 10, 2012.

(51) Int. Cl.
*A61K 38/46* (2006.01)
*A61K 45/06* (2006.01)

(52) U.S. Cl.
CPC ............ *A61K 38/465* (2013.01); *A61K 38/46* (2013.01); *A61K 45/06* (2013.01); *C12Y 301/03005* (2013.01); *C12Y 306/01005* (2013.01)

(58) Field of Classification Search
None
See application file for complete search history.

(56) References Cited

U.S. PATENT DOCUMENTS

| | | | |
|---|---|---|---|
| 2002/0002277 A1* | 1/2002 | Maliszewski .... | C07K 14/70596 536/23.5 |
| 2010/0004178 A1 | 1/2010 | Assaly et al. ................... | 514/12 |
| 2010/0240078 A1* | 9/2010 | Lee .................... | G01N 33/6893 435/7.94 |
| 2011/0039781 A1 | 2/2011 | Schmid-Schonbein et al. ................... | 514/15.2 |
| 2011/0044967 A1 | 2/2011 | Elmaleh et al. ............. | 424/94.3 |

FOREIGN PATENT DOCUMENTS

WO PCT/EP2007/001986 9/2008
WO PCT/EP2009/001603 9/2009

OTHER PUBLICATIONS

Pikkers "Clinical pharmacology of exogenously administered alkaline phosphatase" European Journal of Clinical Pharmacology, (2009), 65:393-402.*
Angus, et al. "Epidemiology of Severe Sepsis in the United States: Analysis of Incidence, Outcome, and Associated Costs of Care" Crit. Care Med. 2001 29:1303-1310.
Ayala, A. & Chaudry, I.H. "Immune Dysfunction in Murine Polymicrobial Sepsis: Mediators, Macrophages, Lymphocytes and Apoptosis" Shock 1996 6:S27-S38.
Benjamim et al. "The Chronic Consequences of Severe Sepsis" J. Leukoc. Biol. 2004 75:408-412.
Blackburn et al. "Metabolic Consequences of Adenosine Deaminase Deficiency in Mice are Associated with Defects in Alveogenesis Pulmonary Inflammation, and Airway Obstruction" J. Exp. Med. 2000 192:159-170.
Bone, R.C. "Immunologic Dissonance: A Continuing Evolution in Our Understanding of the Systemic Inflammatory Response Syndrome (SIRS) and the Multiple Organ Dysfunction Syndrome (MODS)" Ann. Intern. Med. 1996 125:680-687.
Chunn et al. "Partially Adenosine Deaminiase-deficient Mice Develop Pulmonary Fibrosis in Association with Adensoine Elevations" Am. J. Physiol. Lung Cell. Mol. Physiol. 2006 290:L579-L587.
Csóka et al. "$A_{2B}$ Adenosine Receptors Protect Against Sepsis-induced Mortality by Dampening Excessive Inflammation" J. Immunol. 2010 185:542-550.
Deaglio et al. "Adenosine Generation Catalyzed by CD39 and CD73 Expressed on Regulatory T Cells Mediates Immune Suppression" J. Exp. Med. 2007 204:1257-1265.
Eckle et al. "Cardioprotection by Ecto-5'-Nucleotidase (CD73) and $A_{2B}$ Adenosine Receptors" Circulation 2007 115:1581-1590.
Eckle et al. "Identification of Ectonucleotidases CD39 and CD73 in Innate Protection during Acute Lung Injury" J. Immunol. 2007 178:8127-8137.
Eckle et al. "A2B Adenosine Receptor Signaling Attenuates Acute Lung Injury by Enhancing Alveolar Fluid Clearance in Mice" J. Clin. Invest. 2008 118:3301-315.
Eltzschig et al. "Endogenous Adenosine Produced During Hypoxia Attenuates Neutrophil Accumulation: Coordination by Extracellular Nucleotide Metabolism" Blood 2004 104:3986-3992.
Eltzschig et al. "Coordinated Adenine Nucleotide Phosphohydrolysis and Nucleoside Signaling in Posthypoxic Endothelium: Role of Ectonucleotidases and Adenosine $A_{2B}$ Receptors" J. Exp. Med. 2003 198:783-796.
Ernst et al. "Much Ado about Adenosine: Adenosine Synthesis and Function in Regulatory T Cell Biology" J. Immunol. 2010 185:1993-1998.
Fredholm et al. "International Union of Pharmacology. XXV. Nomenclature and Classification of Adenosine Receptors" Pharmacol. Rev. 2001 53:527-552.
Gallos et al. "$A_1$ Adenosine Receptor Knockout Mice Exhibit Increased Mortality, Renal Dysfunction, and Hepatic Injury in Murine Septic Peritonitis" Am. J. Physiol. Renal Physiol. 2005 289:F369-F376.

(Continued)

Primary Examiner — Louise Humphrey
Assistant Examiner — Charles Zoltan Constantine
(74) Attorney, Agent, or Firm — Licata & Tyrell P.C.

(57) ABSTRACT

Methods for attenuating or treating, or reducing the mortality of sepsis or septic shock using an ectonucleotidase such as CD39 or CD73 are provided.

10 Claims, 3 Drawing Sheets

(56) References Cited

OTHER PUBLICATIONS

Gessi et al. "The $A_3$ Adenosine Receptor: An Enigmatic Player in Cell Biology" Pharmacol. Ther. 2008 117:123-140.

Grenz et al. "Protective Role of Ecto-5'-Nucleotidase (CD73) in Renal Ischemia" J. Am. Soc. Nephrol. 2007 18:833-845.

Haskó et al. "Adenosine Receptor Agonists Differentially Regulate IL-10, TNF-α, and Nitric Oxide Production in RAW 264.7 Macrophages and in Endotoxemic Mice" J. Immunol. 1996 157:4634-4640.

Haskó, et al. "Adenosine Inhibits IL-12 and TNF-α Production via Adenosine $A_{2a}$ Receptor-dependent and Independent Mechanisms" FASEB J. 2000 14:2065-2047.

Haskó et al. "Adenosine: A Potential Mediator of Immunosuppression in Multiple Organ Failure" Curr. Opin. Pharmacol. 2002 2:440-444.

Haskó, G. & Cronstein, B.N. "Adenosine: An Endogenous Regulator of Innate Immunity" Trends Immunol. 2004 25:33-39.

Haskó et al. "Adenosine Receptors: Therapeutic Aspects for Inflammatory and Immune Diseases" Nat. Rev. Drug Discov. 2008 7:759-770.

Haskó, G. & Pacher, P. J. "$A_{2A}$ Receptors in Inflammation and Injury: Lessons Learned from Transgenic Animals" Leukoc. Biol. 2008 83:447-455.

Hotchkiss, R.S. & Karl, I.E. "The Pathophysiology and Treatment of Sepsis" N. Engl. J. Med. 2003 348:138-15.

Jacobson, K.A. & Gao, A-G. "Adenosine Receptors as Therapeutic Targets" Nat. Rev. Drug Discov. 2006 5:247-264.

Lee et al. "$A_3$ Adenosine Receptor Activation Decreases Mortality and Renal and Hepatic Injury in Murine Septic Peritonitis" Am. J. Physiol. Regul. Integr. Comp. Physiol. 2006 291:R959-R969.

Lennon et al. "Neutrophil-derived 5'-Adenosine Monophosphate Promotes Endothelial Barrier Function via CD73-mediated Conversion to Adenosine and Endothelial $A_{2b}$ Receptor Activation" J. Exp. Med. 1998 188:1433-1443.

Martin et al. "High Adenosine Plasma Concentration as a Prognostic Index for Outcome in Patients with Septic Shock" Crit. Care Med. 2000 28:3198-3202.

Martin et al. "The Epidemiology of Sepsis in the United States from 1979 through 2000" N. Engl. J. Med. 2003 348:1546-1554.

Montesinos et al. "The Antiinflammatory Mechanisms of Methotrexate Depends on Extracellular Conversion of Adenine Nucleotides to Adenosine by Ecto-5'-Nucleotidase" Arthritis Rheum. 2007 56:1440-1445.

Németh et al. "Adenosine $A_{2A}$ Receptor Inactivation Increases Survival in Polymicrobial Sepsis" J. Immunol. 2006 176:5616-5626.

Németh et al. "Adenosine Stimulates CREB Activation in Macrophages via a p38 MAPK-mediated Mechanism" Biochem. Biophys. Res. Commun. 2003 312:883-888.

Németh et al. "cDNA Microarray Analysis Reveals a Nuclear Factor-κB-Independent Regulation of Macrophage Function by Adenosine" J. Pharmacol. Exp. Ther. 2003 306:1042-1049.

Németh et al "Adenosine Augments IL-10 Production by Macrophages through an $A_{2B}$ Receptor-Mediated Post-transcriptional Mechanism" J. Immunol. 2005 175:8260-8270.

Németh et al. "Adenosine Receptor Activation Ameliorates Type 1 Diabetes" FASEB J. 2007 21:2379-2388.

Oberholzer et al. "Interleukin-10:A Complex Role in the Pathogenesis of Sepsis Syndromes and its Potential as an Anti-inflammatory Drug" Crit. Care Med. 2002 30:S58-S63.

Reutershan et al. "Adenosine and Inflammation: CD39 and CD73 are Critical Mediators in LPS-induced PMN Trafficking into the Lungs" FASEB J. 2009 23:473-482.

Riedemann et al. "The Enigma of Sepsis" J. Clin. Invest. 2003 112:460-467.

Sitkovsky et al. "Physiological Control of Immune Response and Inflammatory Tissue Damage by Hypoxia-inducible Factors and Adenosine $A_{2A}$ Receptors" Annu. Rev. Immunol. 2004 22:657-682.

Synnestvedt et al. "Ecto-5'-nucleotidase (CD73) Regulation by Hypoxia-inducible Factor-1 Mediates Permeability Changes in Intestinal Epithelia" J. Clin. Invest. 2002 110:993-1002.

Thompson et al. "Crucial Role for Ecto-5'-Nucleotidase (CD73) in Vascular Leakage during Hypoxia" J. Exp. Med. 2004 200:1395-1405.

Volmer et al. "Ecto-5'-Nucleotidase (CD73)-Mediated Adenosine Production is Tissue Protective in a Model of Bleomycin-induced Lung Injury" J. Immunol. 2006 176:4449-4458.

Zhong et al. "$A_{2B}$ Adenosine Receptors Increase Cytokine Release by Bronchial Smooth Muscle Cells" Am. J. Respir. Cell Mol. Biol. 2005 32:2-8.

Zhong et al. "Synergy Between $A_{2B}$ Adenosine Receptors and Hypoxia in Activating Human Lung Fibroblasts" Am. J. Respir. Cell Mol. Biol. 2004 30:118-125.

International Search Report and Written Opinion in PCT/US13/54267 dated Jan. 13, 2014.

Haskó et al. "Ecto-5'-Nucleotidase (CD73) Decreases Mortality and Organ Injury in Sepsis" J. Immunol. 2011 187:4256-4267.

International Preliminary Examination Report in PCT/US13/54267 dated Feb. 19, 2015.

* cited by examiner

ATTENUATING OR TREATING SEPSIS OR SEPTIC SHOCK

This application is the National Stage of International Application No. PCT/US2013/054267, filed Aug. 9, 2013, which claims the benefit of priority from U.S. Patent Application Ser. No. 61/681,837, filed Aug. 10, 2012, the contents of each of which are incorporated herein by reference in their entireties.

This invention was made with government support under contract numbers RO1-GM66189 and RO1-A18220 awarded by the National Institutes of Health. The government has certain rights in the invention.

BACKGROUND

Sepsis occurs when microbial invasion induces systemic illness (Bone (1996) *Ann. Intern. Med.* 125:680-687). Despite advances in modern hemodynamic, antibiotic, and ventilatory clinical support, sepsis represents a major clinical problem with no effective therapy (Angus, et al. (2001) *Crit. Care Med.* 29:1303-1310). There are 215,000 deaths related to sepsis in each year in the United States alone (Martin, et al. (2003) *N. Engl. J. Med.* 348:1546-1554; Hotchkiss & Karl (2003) *N. Engl. J. Med.* 348:138-15). Although the pathogenesis of sepsis-induced multiorgan injury leading to death is incompletely understood, it has been suggested that an initial hyperinflammatory process and subsequent immune paralysis contribute to mortality and morbidity in sepsis (Hotchkiss & Karl (2003) supra; Riedemann, et al. (2003) *J. Clin. Invest.* 112:460-467). The initial hyperinflammatory response seen in sepsis is associated with uncontrolled, exuberant cytokine production that can be deleterious to various tissues and can lead to organ injury and dysfunction (Benjamim, et al. (2004) *J. Leukoc. Biol.* 75:408-412; Oberholzer, et al. (2002) *Crit. Care Med.* 30:S58-S63). After this hyperinflammatory phase, an immune paralytic phase ensues with enhanced apoptotic cell death occurring in multiple organs including the spleen, kidney, liver, and heart (Ayala & Chaudry (1996) *Shock* 6:S27-S38).

Adenosine is a biologically active extracellular signaling molecule, which regulates a wide variety of immunological processes by binding to one or more of four G protein-coupled adenosine receptors ($A_1$, $A_{2A}$, $A_{2B}$, and $A_3$) (Németh, et al. (2006) *J. Immunol.* 176:5616-5626; Haskó, et al. (1996) *J. Immunol.* 157:4634-4640; Haskó, et al. (2000) *FASEB J.* 14:2065-2047; Németh, et al. (2003) *Biochem. Biophys. Res. Commun.* 312:883-888; Németh, et al. (2003) *J. Pharmacol. Exp. Ther.* 306:1042-1049; Németh, et al. (2005) *J. Immunol.* 175:8260-8270; Németh, et al. (2007) *FASEB J.* 21:2379-2388; Fredholm, et al. (2001) *Pharmacol. Rev.* 53:527-552; Jacobson & Gao (2006) *Nat. Rev. Drug Discov.* 5:247-264; Sitkovsky, et al. (2004) *Annu. Rev. Immunol.* 22:657-682). Adenosine is produced during inflammation, hypoxia, ischemia, or trauma (Haskó, et al. (1996) supra; Zhong, et al. (2005) *Am. J. Respir. Cell Mol. Biol.* 32:2-8; Chunn, et al. (2006) *Am. J. Physiol. Lung Cell. Mol. Physiol.* 290:L579-L587; Haskó, et al. (2002) *Curr. Opin. Pharmacol.* 2:440-444; Haskó & Cronstein (2004) *Trends Immunol.* 25:33-39; Blackburn, et al. (2000) *J. Exp. Med.* 192:159-170; Zhong, et al. (2004) *Am. J. Respir. Cell Mol. Biol.* 30:118-125), and because sepsis is associated with these metabolically stressful conditions, systemic adenosine levels reach high concentrations in mice and patients with sepsis and septic shock (Martin, et al. (2000) *Crit. Care Med.* 28:3198-3202). There is evidence to suggest that adenosine receptors can regulate the host's response to sepsis. For example, $A_1$, $A_{2B}$, and $A_3$ receptors were found to decrease mortality, inflammation, renal dysfunction, and hepatic injury in murine cecal ligation and puncture (CLP), a clinically relevant model of polymicrobial sepsis (Gallos, et al. (2005) *Am. J. Physiol. Renal Physiol.* 289:F369-F376; Lee, et al. (2006) *Am. J. Physiol. Regul. Integr. Comp. Physiol.* 291:R959-R969; Csóka, et al. (2010) *J. Immunol.* 185:542-550). In contrast, it has been shown that $A_{2A}$ receptor activation contributes to the lethal effect of sepsis via decreased bacterial clearance, increased splenic apoptosis, and insufficient inflammatory cytokine levels (Németh, et al. (2006) supra). Thus, extracellular adenosine is an important regulator of immune events in mice undergoing sepsis and different adenosine receptors can have different and sometimes opposing effects on immunity during sepsis (Haskó & Cronstein (2004) supra; Haskó, et al. (2008) *Nat. Rev. Drug Discov.* 7:759-770; Haskó & Pacher (2008) *J. Leukoc. Biol.* 83:447-455).

One pathway leading to increased extracellular adenosine levels during metabolic stress is release of precursor adenine nucleotides, mostly ATP, from the cell followed by extracellular catabolism to adenosine by a cascade of ectonucleotidases, including CD39 (nucleoside triphosphate diphosphorylase) and CD73 (ecto-5'-nucleotidase) (Thompson, et al. (2004) *J. Exp. Med.* 200:1395-1405; Eltzschig, et al. (2004) *Blood* 104:3986-3992; Eltzschig, et al. (2003) *J. Exp. Med.* 198:783-796; Gessi, et al. (2008) *Pharmacol. Ther.* 117:123-140; Deaglio, et al. (2007) *J. Exp. Med.* 204:1257-1265). CD39 is a transmembrane molecule, which initiates extracellular adenosine generation by catalyzing the degradation of ATP and ADP to AMP (Haskó & Cronstein (2004) supra; Ernst, et al. (2010) *J. Immunol.* 185:1993-1998). CD73 is a 70-kDa glycosyl phosphatidylinositol-anchored cell surface protein with ecto-5'-nucleotidase enzyme activity that catalyzes the dephosphorylation of AMP to adenosine (Lennon, et al. (1998) *J. Exp. Med.* 188:1433-1443; Volmer, et al. (2006) *J. Immunol.* 176:4449-4458). Further, CD73 has been proposed to be the rate-limiting enzyme in the generation of adenosine during metabolic stress (Lennon, et al. (1998) supra; Eckle, et al. (2007) *J. Immunol.* 178:8127-8137). The immune regulatory functions of CD73 are well-documented in several in vivo experimental models. The anti-inflammatory action of methotrexate has been reported to be dependent on the adenosine-producing activity of CD73 (Montesinos, et al. (2007) *Arthritis Rheum.* 56:1440-1445). During LPS-induced acute lung injury, CD73-generated adenosine attenuates LPS-induced polymorphonuclear neutrophil (PMN) trafficking (Reutershan, et al. (2009) *FASEB J.* 23:473-482). Similarly, CD73-derived adenosine protects against bleomycin-induced lung injury (Eckle, et al. (2007) supra) and ventilator-induced acute lung injury (Eckle, et al. (2008) *J. Clin. Invest.* 118:3301-315). In hypoxia models, CD73 activity was required to prevent vascular leak and neutrophil infiltration into various tissues, indicating that extracellular adenosine produced during hypoxia is a potent anti-inflammatory signal for PMNs in vivo (Thompson, et al. (2004) supra; Synnestvedt, et al. (2002) *J. Clin. Invest.* 110:993-1002). A protective role of CD73-generated adenosine has also been shown in renal and myocardial ischemia (Grenz, et al. (2007) *J. Am. Soc. Nephrol.* 18:833-845; Eckle, et al. (2007) *Circulation* 115:1581-1590). Moreover, the use of alkaline phosphatase, CD39 and CD37 in the prophylaxis of a mammal at risk of inflammatory diseases has been suggested (WO 2008/104200 and WO 2009/106368).

SUMMARY OF THE INVENTION

This invention provides a method for attenuating or treating sepsis or septic shock by administering an effective amount of at least one ectonucleotidase to a subject in need thereof. The invention also provides a method for reducing mortality associated with sepsis or septic shock by administering an effective amount of at least one ectonucleotidase. In accordance with some embodiments of the instant methods, the ectonucleotidase is CD73, CD39, a non-human apyrase, an enhanced apyrase, or a combination thereof. In other embodiments, the ectonucleotidase is administered with an osmolyte. In further embodiments, the methods further include the administration of an antibiotic, an anti-inflammatory agent, activated protein C, insulin, or a combination thereof.

DETAILED DESCRIPTION OF THE INVENTION

Figure 1A:
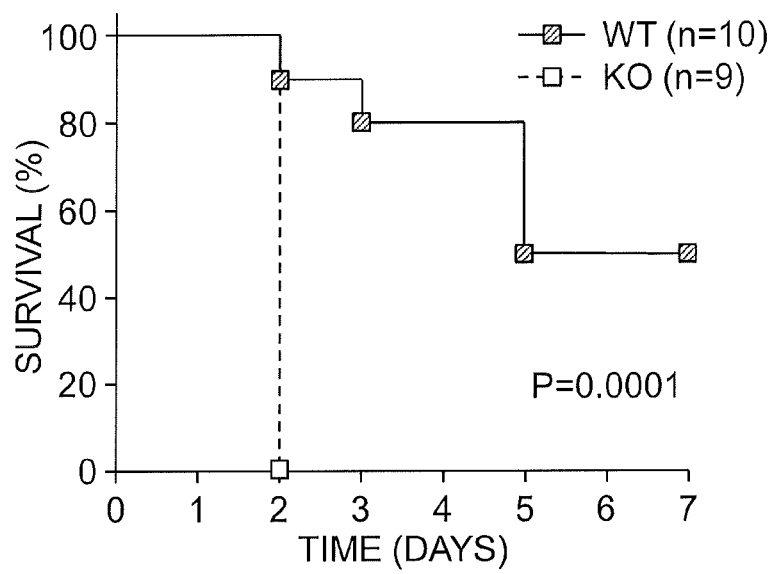
FIGS. 1A-1C show the effects of a CD39 knockout on septic mortality and plasma cytokine levels in C57BL/6J mice. Wild-type (WT) and CD39 knockout (KO) mice were subjected to CLP insult. Animals were resuscitated with 1 ml of physiological saline immediately after CLP and survival was monitored (FIG. 1A). TNF-α (FIG. 1B) and MIP-2 (FIG. 1C) were measured 16 hours post-CLP. $*p<0.05$.

Sepsis results in the release of nucleotides, such as ATP and ADP, from the intracellular space to the extracellular space. Extracellular adenosine triphosphate (ATP) and adenosine diphosphate (ADP) are signaling molecules that act on P2 purinergic receptors to modulate a plethora of physiological and pathophysiological processes. In general, ATP and ADP are considered harmful, proinflammatory mediators. However, ATP and ADP are short-lived in the extracellular space because their phosphate groups are removed by ectonucleotidases to produce adenosine monophosphate (AMP) and adenosine. Although AMP is an inactive metabolite, adenosine is an extracellular signaling molecule that has wide-ranging effects on cells, tissues and organs by binding to P1 purinergic or adenosine receptors. In general, adenosine is viewed as a protective, anti-inflammatory mediator.

It has now been found that supplementation with the exogenous ectonucleotidase, apyrase, decreases mortality and prevents organ dysfunction in a murine model of septic shock induced by the cecal ligation and puncture technique. The results herein demonstrate the utility of ectonucleotidase modulation in protecting against sepsis and septic shock. Therefore, the present invention provides the use of supplemental ectonucleotidases to metabolize extracellular nucleotides to AMP and adenosine in the treatment of sepsis. In addition, screening assays can be carried out to identify small organic molecules, antibodies, peptides, small interfering RNAs, antisense RNA, and other agents that modulate ectonucleotidase activity. The constellation of extracellular nucleotides and nucleosides (adenosine) has been shown to be anti-inflammatory and beneficial in various pathophysiological situations. Therefore, the present findings are applicable to a number of inflammatory conditions.

The extracellular release of adenosine can occur via two distinct mechanisms, either directly via cell membrane embedded adenosine/nucleoside transporters or indirectly, as a constituent of the nucleotides ATP and ADP, which can be released by a number of mechanisms, including membrane damage, through connexin/pannexin and other channels (Eltzschig, et al. (2006) *Circ. Res.* 99:1100-1108), and via protein or hormone-transporting vesicles. Following the release of ATP and ADP, the phosphate groups are sequentially cleaved by a cascade of ecto-enzymes on the cell surface to produce adenosine. It is now widely accepted that the dominant enzyme that catalyzes the extracellular hydrolysis of ATP and ADP is ectonucleoside triphosphate diphosphohydrolase 1 (E-NTPDase1 or CD39). This enzyme produces AMP, which is then metabolized to adenosine by ecto-5'-nucleotidase (Ecto5'NTase or CD73). The entire catalytic pathway is complete in a few hundred milliseconds, and the rate-limiting step appears to be the dephosphorylation of AMP to adenosine by CD73.

CD39 is the most prominent member of the cell surface E-NTPDase family. It has two membrane-spanning domains at its N- and C-termini and its extracellular domain contains five apyrase conserved regions, which are responsible for its catalytic activity. CD39 is widely expressed, whereas other E-NTPDases are localized to neural tissue or pericytes. CD39 is the major nucleotide-metabolizing enzyme in peripheral blood leukocytes, spleen, lung, and placenta, and is expressed on macrophages, neutrophils, Tregs, Langerhans cells, and endothelial cells.

CD73 is a cell surface-associated ecto-5'-nucleotidase and is anchored to the plasma membrane at the C-terminus by glycosyl-phosphatidylinositol (GPI). CD73 is readily detected on cells from blood, spleen, lymph nodes, bone marrow, and endothelium, and, within the immune system, CD73 is found on the surface of macrophages, lymphocytes, including Treg cells in mice, and dendritic cells. There is evidence that the expression and function of both CD39 and CD73 on endothelial cells is upregulated following hypoxia, and exposure to TGF-β increases the expression of CD39 on T cells.

It has been demonstrated that adenosine produced as a result of the coordinated action of CD39 and CD73 is involved in protecting organs against hypoxic and ischemic insults. Early studies using both genetic knockout (KO) and pharmacological inhibition of CD39 and CD73 in mice showed that these enzymes mediate protection against increased vascular permeability and neutrophil extravasation during ambient hypoxia, wherein increased vascular permeability and neutrophil extravasation in CD39 and CD73 KO mice could be reversed by stimulating adenosine receptors with exogenous administration of 5'-(N-ethylcarboxamido)adenosine (NECA), a general adenosine receptor agonist, or by exogenous reconstitution with soluble forms of CD39 (apyrase) and CD73 (5'-nucleotidase). These results were later extended to models of organ-specific ischemia/reperfusion, where in CD39 or CD73 KO mice the organ injury and inflammation that followed cardiac, renal, hepatic, and intestinal ischemia were more severe than in the corresponding wild-type mice.

Adenosine may also be central to preventing tissue injury caused by nonischemic inflammatory insults. For example, it has been shown that vascular injury induces increased monocyte arrest, nuclear factor κB (NF-κB) accumulation and adhesion molecule expression in CD73 KO versus wild-type mice. This increased inflammation in CD73 KO mice was readily reversed by treatment with an adenosine receptor agonist. In other studies, lipopolysaccharide (LPS)-induced neutrophil trafficking to the lung was exacerbated in the genetic absence or after pharmacological inhibition of CD39 or CD73 and this increased lung inflammation was attenuated by administering soluble CD39 or CD73. In addition, a further study demonstrated that CD73 KO mice displayed increased migration of lymphocytes to draining lymph nodes upon LPS administration, which was normalized by treatment with an adenosine receptor agonist. Further, inactivation of CD73 was shown to promote atherosclerosis by de-inhibition of resident macrophages.

Adenosine is a significant mediator of the anti-inflammatory and immunosuppressive function of murine Treg cells. CD39 and CD73 are highly expressed on the surface of Foxp3+ Treg cells and have been increasingly used as markers of Tregs. Functionally, using KO mice, it has been shown that the coexpression of CD39 and CD73 with the pericellular generation of adenosine dictates a substantial component of the immune suppressive and anti-inflammatory capabilities of Treg cells.

It has been further demonstrated that CD73 improves the survival of mice made septic by cecal ligation and puncture, and that this improved survival correlates with a decrease in bacterial growth and lessened organ injury (Haskó, et al. (2011) *J. Immunol.* 187:4256-4267). It was observed that the survival rate of wild-type mice was significantly higher than that of CD73 KO animals. This increased survival of wild-type versus CD73 KO mice was associated with decreased inflammatory cytokine levels, lung and kidney injury, neutrophil infiltration into the lung, and NF-κB activation. These results, suggest that CD73 is a control point in limiting inflammation during sepsis. To confirm that adenosine signaling is responsible for the CD73-mediated decrease in inflammation, a series of studies were conducted in which an attempt was made to rescue CD73 KO mice from decreased adenosine signaling by stimulating adenosine receptors exogenously with the general adenosine receptor agonist NECA. Administration of NECA to CD73 KO mice completely reversed the increased cytokine levels, decreasing them to levels comparable to those observed in wild-type mice. It was concluded that the decreased inflammatory response observed in wild-type versus CD73 KO mice was caused by adenosine receptor signaling.

Figure 1B:
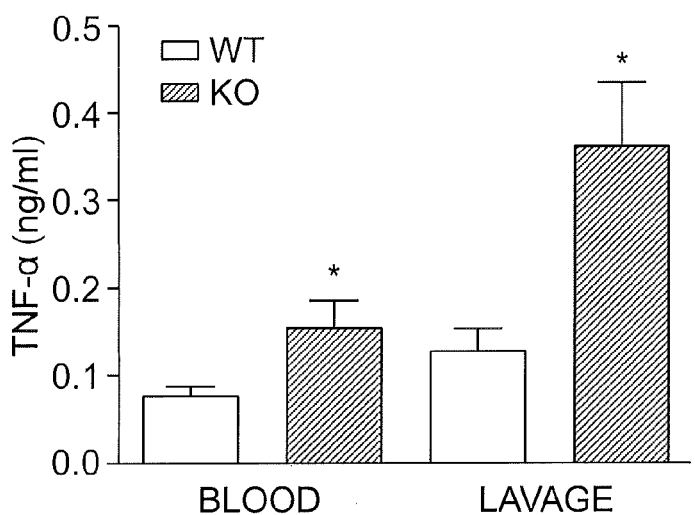
Figure 1C:
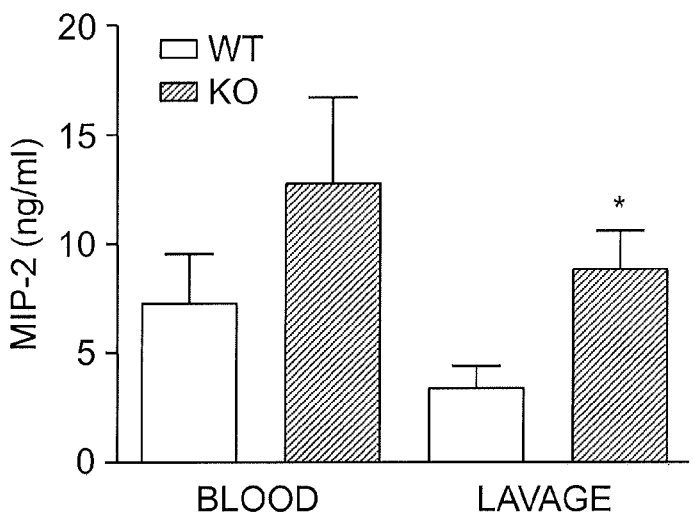
Figure 2A:
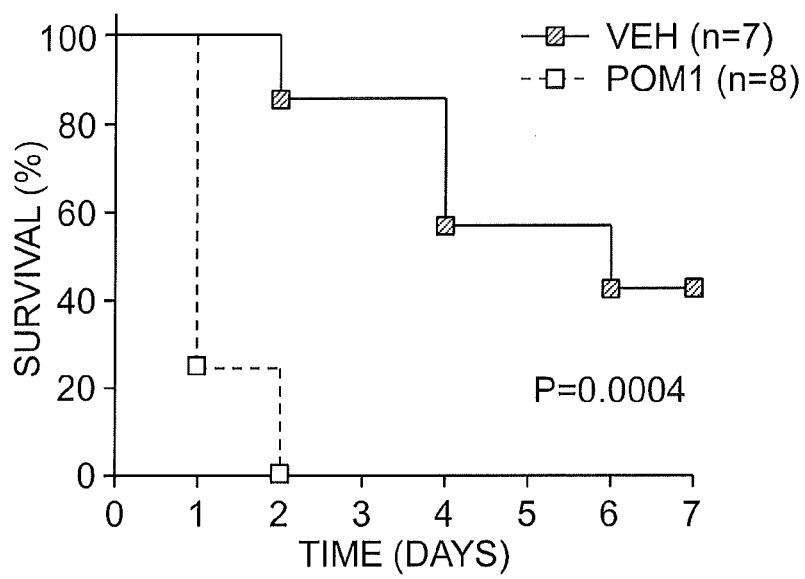
FIGS. 2A-2C show the effects of a CD39 pharmacological blocker, sodium polyoxotungstate (POM1), on septic mortality and plasma cytokine levels in C57BL/6J mice. POM1 was administered before the CLP insult. Mice were subjected to CLP insult and animals were resuscitated with 1 ml of physiological saline immediately after CLP. TNF-α and MIP-2 were measured 16 hours post-CLP. $*p<0.05$; $p<0.01$; $*p<0.001$ vs. vehicle (VEH).
Figure 2B:
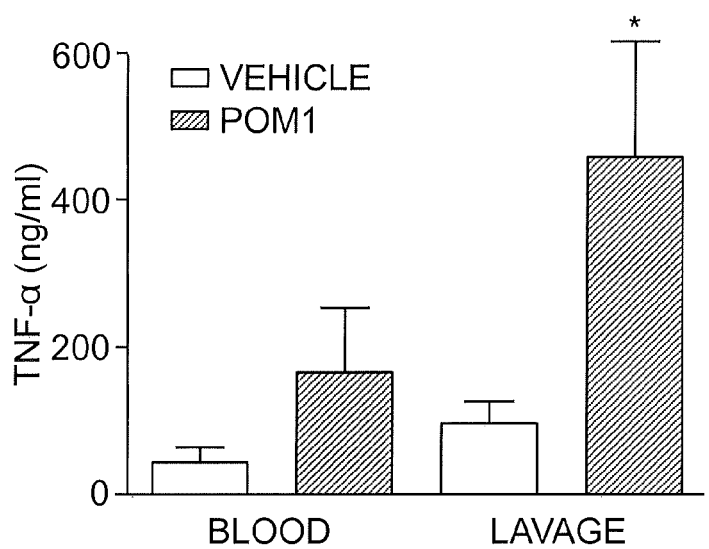
Figure 2C:
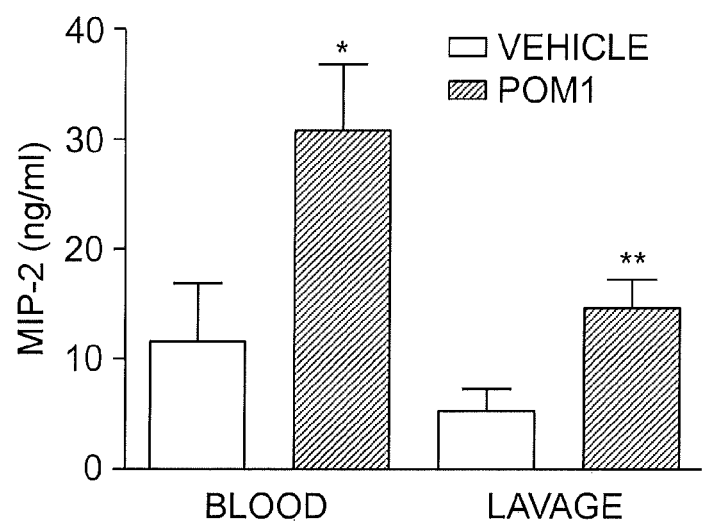
Figure 3A:
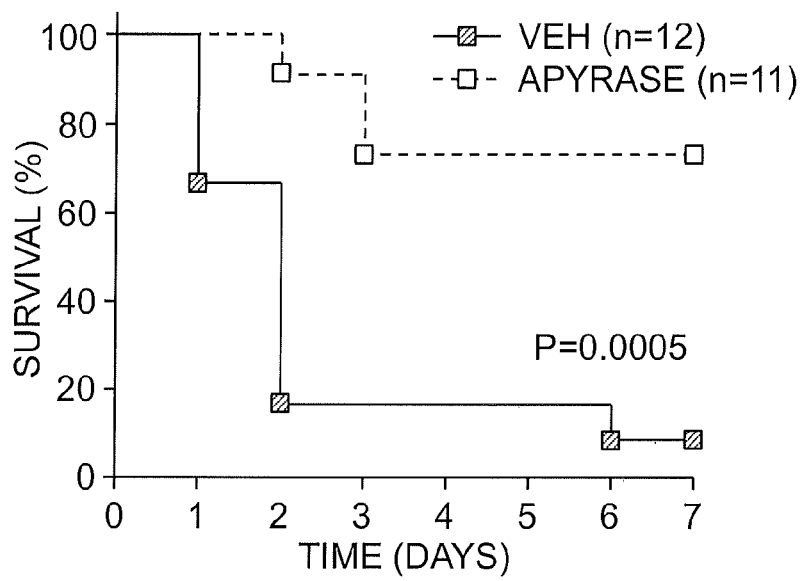
FIGS. 3A-3C show that apyrase protects against septic mortality and decreases plasma cytokine levels in C57BL/6J mice. Apyrase (250 U/kg) was administered intraperitoneally 30 minutes before the CLP insult and then every 24 hours thereafter. Animals were resuscitated with 1 ml of physiological saline immediately after CLP. TNF-α and MIP-2 were measured 16 hours post-CLP. $*p<0.05$; $p<0.01$; $*p<0.001$ vs. vehicle; n=10.
Figure 3B:
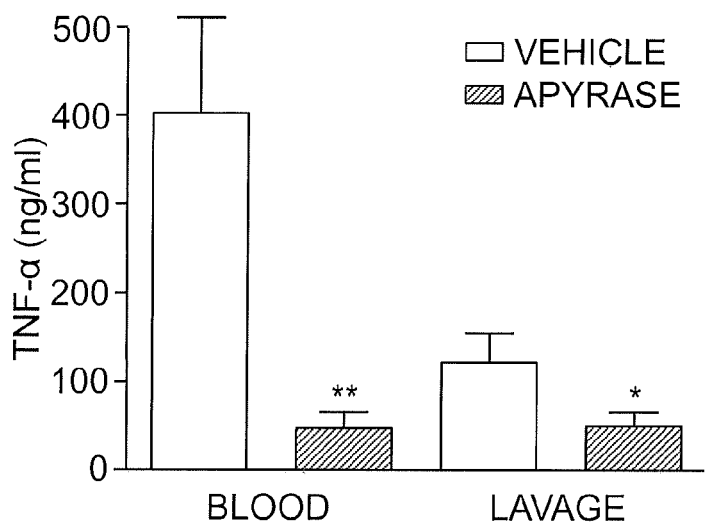
Figure 3C:
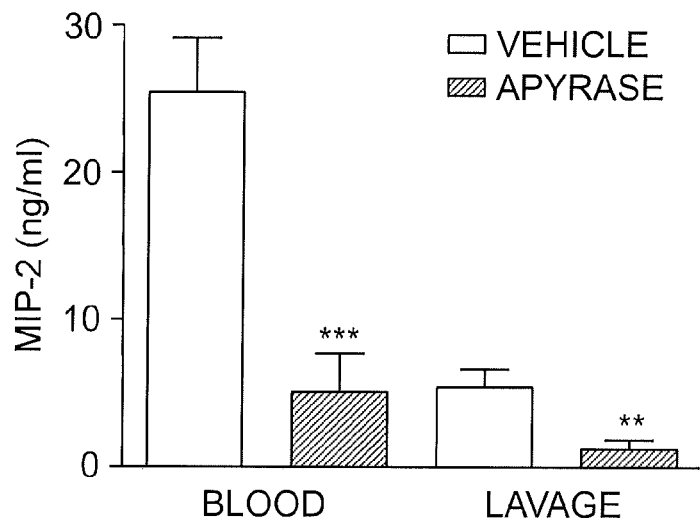

While it has been suggested that ectonucleotidases play a role in controlling inflammation via decreasing extracellular ATP and ADP and increasing extracellular adenosine concentrations, a definitive association between ectonucleotidases and inflammation associated with sepsis has not been demonstrated. Therefore, experiments were conducted to demonstrate a role for ectonucleotidases in inflammation associated with sepsis. In this analysis, CD39 KO mice, mice administered a CD39 blocker (sodium polyoxotungstate) or mice administered an apyrase (potato apyrase) were made septic by cecal ligation and puncture (CLP) and survival after CLP was recorded for 7 days. In addition, the immune status of the mice was assessed by measuring cytokine levels from blood and peritoneal lavage fluid. This analysis indicated that whereas CD39 KO (FIG. 1A) or CD39 inhibition (FIG. 2A) exacerbated sepsis in the mouse model, apyrase administration (FIG. 3A) led to improved survival in C57BL16J mice. In addition, whereas CD39 KO (FIGS. 1B and 1C) and CD39 inhibition (FIGS. 2B and 2C) increased the levels of the harmful proinflammatory cytokines tumor necrosis factor (TNF)-α and macrophage inflammatory protein (MIP)-2, apyrase administration (FIGS. 3B and 3C) decreased the levels of these cytokines. These results definitively demonstrate that ectonucleotidase supplementation by apyrase administration protects against septic mortality and inflammation. Thus, ectonucleotidase manipulation is therapeutically useful for the treatment of septic shock.

Accordingly, the present invention provides a method for attenuating or treating sepsis or septic shock by administering one or more exogenous or supplemental ectonucleotidases or agents that stimulate the expression or activity of endogenous ectonucleotidases. As is conventional in the art, sepsis is defined as a Systemic Inflammatory Response Syndrome to an infective process in which severe derangement of the host immune system fails to prevent extensive 'spill over' of inflammatory mediators from a local infection focus into the systemic circulation. The diagnosis of sepsis is based on the presence of at least two out of the following four criteria: tachycardia (heart rate>90 bpm), hyperventilation (respiratory frequency>20/min or $pCO_{2exp}$<35 mmHg), fever (>38.3° C.) or hypothermia (<36° C.) and leukocytosis (>12,000/μL) or leukopenia (<4,000/μL).

Infection is suspected when physiologic manifestations present, such as white blood cells (WBCs) noted in a normally sterile body fluid, perforated viscus, chest radiograph consistent with pneumonia, or a clinical syndrome associated with a high likelihood of infection (e.g., ascending cholangitis). Evidence of a systemic inflammatory response includes derangement in vital signs and WBC count. Physiologically, sepsis is characterized by cytokine release, increased expression of adhesion molecules, release of reactive oxygen species, and expression of acute-phase proteins.

Infections associated with sepsis can lead to a shock, called septic shock. The term "septic shock," as used herein, is a consequence of sepsis in which the systemic inflammatory response leads to the failure of vital organs' function (for example of the lungs as in acute respiratory distress syndrome (ARDS)). A significant feature of septic shock is that the failure of vital organ function has not occurred yet but is in progress and will occur within a short period of time.

For the purposes of this invention, an ectonucleotidase is a subclass of phosphatases which function extracellularly, i.e., are capable of dephosphorylating an extracellular substrate in the extracellular space. This in contrast with intracellular phosphatases (i.e., kinases) that dephosphorylate intracellular substrate inside the cell, i.e., the intracellular space. Ectonucleotidases of use in this invention include, but are not limited to ectonucleoside triphosphate diphosphohydrolases (NTPDases; EC 3.6.1.5) such as NTPDases 1-8 and ecto-5'-nucleotidases (EC 3.1.3.5) such as CD73. See Shirley et al. (2009) *Purinergic Signal.* 5:501-511.

In some embodiments, the ectonucleotidase is CD73. In other embodiments, the ectonucleotidase is an NTPDase. In particular embodiments, the ectonucleotidase is an NTP- Dase such as CD39 (NTPDase1 or human apyrase; see GENBANK Accession Nos. NP_001767, NP_001091645, NP_001157650, NP_001157651, NP_001157653, and NP_001157655, which disclose isoforms 1-6), human NTP-Dase3 (GENBANK Accession NO. NP_001239), a non-human apyrase, or an enhanced apyrase with improved therapeutic properties such as longer half-life, higher stability, or higher solubility, or higher purity (see US 2013/0142775). In certain embodiments, more than one ectonucleotidase is administered. In accordance with this embodiment, CD73 can be administered in combination with CD39, a non-human apyrase, or an enhanced apyrase. Alternatively, two different apyrases may be administered, for example, CD39 and a non-human apyrase (e.g., potato apyrase); CD39 and an enhance apyrase; or a non-human apyrase (e.g., potato apyrase) and an enhance apyrase.

The non-human apyrase according to the present invention can be a naturally occurring apyrase such as an apyrase found in microbial species such as *E. coli, Aspergillus fumigatus* and *Kluyveromyces lactis*, in plants species such as *Arabidopsis thaliana, Glycine max* and *Oryza sativa*, in insects species such as *Drosophila melanogaster* and in mammals like *Rattus norvegicus* and *Mus musculus*. In other embodiments, the source of apyrase is potato. Potato, and preferably genetically modified potato producing a non-membrane bound apyrase (ecto-apyrase), allows the isolation of large quantities of apyrase using a relative simple and economic method.

Ectonucleotidases are available from a number of commercial sources including, e.g., Sigma and New England Biolabs. Alternatively, the ectonucleotidase can be isolated from a source of interest (i.e., a purified ectonucleotidases), or synthetically or recombinantly produced. For example, using PCR primers based on the known apyrase DNA sequences, preferably of human origin, nucleic acid amplification techniques can be used for the identification, isolation, cloning and modification (e.g., site directed mutagenesis) of the coding sequence of an ectonucleotidase. Once isolated, the coding sequence can be placed under the control of appropriate regulation signals and transformed in a suitable host allowing the expression and isolation of the enzyme.

In certain embodiments, a synthetic or recombinant ectonucleotidase is engineered to have improved physicochemical properties such as improved solubility, thermal or mechanical stability, proteolytic resistance, and/or circulating half-life; and/or reduced antigenicity, immunogenicity, and/or toxicity. For example, protein solubility may be improved by replacing one or more less favorable hydrophilic residues (e.g., asparagine, glutamine, threonine, lysine, and arginine) with more favorable hydrophilic residues (e.g., aspartic acid, glutamic acid, and serine). See Trevino, et al. (2008) *J. Pharma. Sci.* 97:4155-66. Further, protein structure analysis has shown that glycine, serine, serine, lysine and aspartic acid in mesophilic proteins are respectively substituted by alanine, alanine, threonine, arginine and glutamic acid in thermophilic proteins (see Argos, et al. (1979) *Biochemistry* 18:5698-5703). Thermostability can also be improved by ligation to a thermostable domain (Fu, et al. (2005) *Biotechnol. Prog.* 21:1429-35) or by grafting the catalytic domain of the ectonucleotidase to a scaffold that has been chosen or designed specifically for high thermostability (Kuhlman, et al. (2003) *Science* 302: 1364-1368; Feldwisch, et al. (2010) *J. Mol. Biol.* 398:232-247; Kolmar (2009) *Curr. Opin. Pharmacol.* 9:608-614; Garcia & Camarero (2010) *Curr. Mol. Pharmacol.* 3:153-163).

In particular embodiments of the present invention, the ectonucleotidase is a soluble ectonucleotidase. In most cases, this would mean a deletion of the transmembrane and/or intracellular domain while leaving the catalytic part of the extracellular part of the enzyme functionally intact.

In accordance with the present invention, the ectonucleotidase is of use for the preparation of a medicament for the attenuation or treatment of a mammal, preferably a human mammal, at risk of or suffering from sepsis or septic shock. The term "attenuation," as used herein, is used to indicate a measure taken for the prevention or prophylaxis of a disease or condition, in the present case minimizing, reducing or suppressing the risk of developing, or parameters relating to, sepsis or septic shock. The term "treating" or "treatment," as used herein, refers to an improvement or remediation of the symptoms associated with sepsis, septic shock or consequences thereof. The improvement is an observable or measurable improvement. Thus, one of skill in the art realizes that a treatment may improve the disease condition, but may not be a complete cure for the disease. Accordingly, the present use of ectonucleotidases relates to administering the present medicament to a mammal, and especially a human mammal, suffering from, or at risk of, sepsis or septic shock. In accordance with the present invention, administration of a supplemental ectonucleotidase results in a measurable reduction in pro-inflammatory cytokine levels (e.g., TNF-$\alpha$ and MIP-2) and reduced mortality in subjects with or at risk of sepsis or septic shock. As such, the present invention also provides a method for reducing mortality associated with sepsis or septic shock using supplemental ectonucleotidase. The term "mortality," as used herein, is the state of being mortal or causing death. Yet further, mortality can also refer to the death rate or the ratio of number of deaths to a given population.

CD39 and CD73 supplementation, in accordance with the present invention, has the advantage of locally releasing adenosine and targeting adenosine receptors at sites of injury in affected organs where nucleotides (i.e., ATP and ADP) are released. This provides an opportunity for interventions that have fewer systemic side effects than adenosine receptor ligands, which can cause hypotension or respiratory problems. Ectonucleotidase supplementation is particularly appealing for patients undergoing cardiac bypass surgery who often sustain permanent ischemia-induced kidney damage and for patients suffering from sepsis, given the high rate of mortality in these individuals.

One skilled in the art can determine the effective amount or therapeutically effective amount of a supplemental ectonucleotidase, i.e., an amount that results in an improvement or attenuation of the symptoms of sepsis or septic shock, to be administered to a subject based upon several considerations, such as local effects, pharmacodynamics, absorption, metabolism, method of delivery, age, weight, disease severity and response to the therapy. Typical amounts for administration are from about 1 mg to about 300 g per day, preferably about 3 mg to about 100 g per day, and, in particular, 3 g to about 20 g per day. Alternatively, effective amounts are between 10 to 400 IU/kg body weight, wherein one IU unit is defined as the amount of ectonucleotidase capable of liberating 1 micromole of inorganic phosphate from ATP or ADP per minute at pH 6.5 at 30° C. Administration is effected preferably 3 times a day, for example, at doses of 0.5 to 10 g each, preferably 1 to 5 g, even more preferably 1.5 to 3 g per administration. The ectonucleotidase may also be given as a continuous infusion via a nasogastric tube.

The ectonucleotidase may be administered by either enteral or parenteral administration. Enteral administration includes oral, sublingual, intragastric and rectal routes. Parenteral routes include intravenous, subcutanous, intraperitoneal or inhalation.

For prophylactic or therapeutic purposes, the ectonucleotidase can be administered as a pharmaceutical composition containing a therapeutically effective amount of the ectonucleotidase and one or more pharmaceutically acceptable excipients and/or carriers. Solid, semi-solid, e.g., pastes, or liquid pharmaceutical compositions as well as other dosage forms and the preparation thereof, are well-established and for instance described in Gennaro et al., Remington's Pharmaceutical Sciences (20$^{th}$ Ed., Lippincott Williams & Wilkins, Baltimore, USA).

The term "carrier" refers to a diluents or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Typical pharmaceutical compositions and dosage forms include one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents In particular embodiments, the ectonucleotidase is provided in a composition containing an osmolyte, which increases the stability of the ectonucleotidase. An "osmolyte," as used herein, refers to any organic or inorganic compound or the like, which has the ability to increase the thermal stability of an ectonucleotidase. Osmolytes that protect proteins can be divided into three classes (Somero & Yancey (1997) in *Handbook of Physiology*, Hoffman & Jamieson, Eds., pp. 441-484. Oxford University Press): (i) sugars and polyhydric alcohols (polyoles), (ii) amino acids and amino acid derivatives, and (iii) methylated ammonium and sulfonium compounds. Osmolytes of group (i) include, for example, trehalose, floridoside, glycerol, pinitol, sorbitol and myo-inisitol. Group (ii) includes, for example, alanine, β-alanine, proline, ectoine, taurine, $N_\epsilon$-acetyl-β-lysine, $N_\alpha$-carbamoyl-L-glutamine-l-amide. Group (iii) includes, for example, trimethylamine-N-oxide, glycerophosphoryl choline, proline betaine, β-alanine betaine, glycine betaine, choline-O-sulfate, homarine and dimethyl-sulfoniopropionate. All these compounds are included in the scope of the invention. In one embodiment, the osmolyte is glycine betaine. See WO 2004/035818.

The suitable concentration for the osmolyte that is used is readily determined by a person skilled in the art. However, for the purposes of the invention, the concentration of the osmolyte(s) is, for example, in the interval from 0.1 to 10 M, preferably from 0.5 to 2M. Also, a combination of different osmolytes may be used, whereby different osmolytes may contribute with different physical properties.

In order to increase the effectiveness of the composition, it may be desirable to combine the ectonucleotidase composition and method of the invention with a known agent effective in the treatment or prevention of bacteremia, sepsis, septic shock and related conditions, for example known agents to treat bacterial infections, e.g., antibiotics. The composition of the present invention may precede, be co-current with and/or follow the other agent(s) by intervals ranging from minutes to weeks. In embodiments where the composition of the present invention, and other agent(s) are applied separately, one would generally ensure that a significant period of time did not expire between the time of each delivery, such that the composition and agent(s) would still be able to exert an advantageously combined effect.

Non-limiting examples of other agents that may be used in the present invention include antimicrobial agents, anti-inflammatory agents, activated protein C (e.g., drotrecogin alpha(activated)), insulin or a combination thereof. In certain aspects of the present invention, antimicrobial agents, e.g., antibiotics are used in combination with the composition of the present invention. Examples of specific antibiotics that can be used include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in U.S. Pat. No. 4,642,104, can be used. Anti-inflammatory agents include, but are not limited to non-steroidal anti-inflammatory agents (e.g., naproxen, ibuprofen, celeoxib) and steroidal anti-inflammatory agents (e.g., glucocorticoids).

In addition to prevention and treatment, the present invention also provides a method of identifying an agent of use in the prevention or treatment of sepsis or septic shock based on the ability of the agent to increase, promote or potentiate the expression or activity of an ectonucleotidase. This method of the invention involves (a) exposing a cell expressing CD39 and/or CD73 to a test agent and (b) assaying CD39 and/or CD73 biological activity, wherein an increase in CD39 and/or CD73 biological activity in the cell, relative to CD39 and/or CD73 biological activity in a cell not exposed to the test agent, indicates that the agent is potentially of use in the prevention or treatment of sepsis or septic shock. In some embodiments, CD39 biological activity is the phosphohydrolysis of nucleoside diphosphate (e.g., ADP or UDP) or triphosphate (e.g., ATP OR UTP). In other embodiments, CD73 biological activity is the phosphohydrolysis of a nucleoside monophosphate (e.g., AMP). In yet another embodiment, the cell is a monocyte, macrophage, endothelial cell, or cancer cell.

By "increase," "promote," or "potentiate" is meant that an agent is able to enhance the expression of a gene encoding a polypeptide, increase the activation of a polypeptide, or increase the biological activity of a polypeptide that functions as an ectonucleotidase, e.g., CD39 or CD73, by at least 5%, more desirably, by at least 10%, even more desirably, by at least 25%, 50%, or 75%, and most desirably, by 90% or more as determined using a conventional NTPDase or ecto-5'-nucleotidase assay. Alternatively, an agent can prevent downregulation, degradation or clearance of an ectonucleotidase thereby increasing, promoting or potentiating the expression or activity of an ectonucleotidase.

Agents that can be screened in accordance with the present method include any naturally occurring molecule such as a biological macromolecule (i.e., nucleic acid, protein, non-peptide, or organic molecule), or an extract made from biological materials such as bacteria, plants, fungi, or animal (particularly mammalian) cells or tissues; or a non-naturally occurring molecule such as a small organic molecule from a library of synthetic compounds.

The invention is described in greater detail by the following non-limiting examples.

Example 1: Materials and Methods

Experimental Animals.

CD39 knockout (KO) mice and their wild-type littermates were developed according to established methods and were backcrossed 6-8 times to a C57BL/6J background (Enjyoji, et al. (1999) *Nat. Med.* 5(9):1010-7). Wild-type and KO littermates were used in this analysis. In some experiments, mice were treated with sodium polyoxotungstate (POM-1, $Na_6[H_2W_{12}O_{40}]$, 3 mg/kg/h, i.e., prior to CLP) or apyrase from potatoes (Sigma, 5 U apyrase i.p., prior to CLP).

Sepsis Induction by CLP.

Polymicrobial sepsis was induced by subjecting C57BL/6J mice to CLP in accordance with established methods (Németh, et al. (2006) supra; Gallos, et al. (2005) supra; Lee, et al. (2006) supra; Csóka, et al. (2010) supra). After the operation, all mice were resuscitated with 1 ml physiological saline injected s.c. and returned to their cages with free access to food and water.

Collection of Blood and Peritoneal Lavage Fluid.

Sixteen hours after the CLP operation (the following day), the mice were reanesthetized with pentobarbital (50 mg/kg i.p.), and blood and peritoneal lavage fluid were harvested. Specifically, after opening the chest of mice, blood samples were obtained aseptically by cardiac puncture using heparinized syringes. Blood samples were then placed into heparinized EPPENDORF tubes and kept on ice until used. To collect peritoneal lavage fluid, the abdominal skin was first cleansed with 70% ethanol and then the abdominal wall was exposed by opening the skin. Two milliliters of sterile physiological saline was slowly injected into the peritoneal cavity via an 18-gauge needle. The abdomen was gently massaged for 1 minute while keeping the tip of the needle in the peritoneum. Subsequently, the peritoneal fluid was recovered through the needle, and the recovered peritoneal lavage fluid was placed on ice until used.

Determination of Cytokine Levels.

Concentrations of TNF-α and MIP-2 were determined in blood and peritoneal lavage fluid obtained 16 hours after CLP using commercially available ELISA kits (R&D Systems, Minneapolis, Minn.) according to the manufacturer's instructions.

What is claimed is:

1. A method for attenuating or treating sepsis or septic shock comprising administering at least one ectonucleotidase to a subject in need thereof in an amount effective to limit inflammation during sepsis thereby attenuating or treating the subject's sepsis or septic shock, wherein the ectonucleotidase is selected from the group consisting of an ecto-nucleoside triphosphate diphosphohydrolase 2 (E-NTPDase2), an E-NTPDase3, an E-NTPDase4, an E-NTPDase5, an E-NTPDase6, an E-NTPDase7, E-NTPDase8, an ecto-5'-nucleotidase and a non-human apyrase, or a combination thereof.

2. The method of claim 1, wherein the ectonucleotidase is selected from the group consisting of the ecto-5'-nucleotidase CD73, E-NTPDase3 and a non-human apyrase, or a combination thereof.

3. The method of claim 2, wherein the subject is administered CD73 and E-NTPDase3 or a non-human apyrase, or a combination thereof.

4. The method of claim 1, wherein the ectonucleotidase is administered with an osmolyte.

5. The method of claim 1, further comprising administering an antibiotic, an anti-inflammatory agent, activated protein C, insulin, or a combination thereof.

6. A method for reducing mortality associated with sepsis or septic shock comprising administering at least one ectonucleotidase to a subject in need thereof in amount effective to limit inflammation during sepsis thereby reducing mortality associated with sepsis or septic shock, wherein the ectonucleotidase is selected from the group consisting of an ecto-nucleoside triphosphate diphosphohydrolase 2 (E-NTPDase2), an E-NTPDase3, an E-NTPDase4, an E-NTPDase5, an E-NTPDase6, an E-NTPDase7, an E-NTPDase8 an ecto-5'-nucleotidase and a non-human apyrase, or a combination thereof.

7. The method of claim 6, wherein the ectonucleotidase is selected from the group consisting of the ecto-5-nucleotidase CD73, E-NTPDase3 and a non-human apyrase, or a combination thereof.

8. The method of claim 7, wherein the subject is administered CD73 and E-NTPDase3 or a non-human apyrase, or a combination thereof.

9. The method of claim 6, wherein the ectonucleotidase is administered with an osmolyte.

10. The method of claim 6, further comprising administering an antibiotic, an anti-inflammatory agent, activated protein C, insulin, or a combination thereof.

* * * * *